United States Patent [19]

Reichmann et al.

[11] 4,146,550

[45] Mar. 27, 1979

[54] PROCESS FOR THE PREPARATION OF AN ALIPHATIC MONOISOCYANATE

[75] Inventors: Wolfgang Reichmann, Dusseldorf; Klaus König, Leverkusen, both of Fed. Rep. of Germany

[73] Assignee: Bayer Aktiengesellschaft, Leverkusen, Fed. Rep. of Germany

[21] Appl. No.: 817,082

[22] Filed: Jul. 18, 1977

[30] Foreign Application Priority Data

Aug. 5, 1976 [DE] Fed. Rep. of Germany ....... 2635280
Jan. 19, 1977 [DE] Fed. Rep. of Germany ....... 2702051

[51] Int. Cl.$^2$ ........................................... C07C 118/00
[52] U.S. Cl. ................................................ 260/453 P
[58] Field of Search ...................... 260/453 P, 453 PH

[56] References Cited

U.S. PATENT DOCUMENTS

| | | | |
|---|---|---|---|
| 2,773,086 | 12/1956 | Slocombe et al. | 260/453 P |
| 3,410,887 | 11/1968 | Saviah et al. | 260/453 PH |
| 3,852,317 | 12/1974 | Zanker | 260/453 P |
| 3,860,623 | 1/1975 | Zanker et al. | 260/453 P |
| 4,003,938 | 1/1977 | Koenig et al. | 260/453 P |

*Primary Examiner*—Dolph H. Torrence
*Attorney, Agent, or Firm*—Gene Harsh; Joseph C. Gil

[57] ABSTRACT

This invention relates to an improved process for the preparation of an aliphatic monoisocyanate from the corresponding carbamic acid chloride. The carbamic acid chloride is reacted with an active hydrogen compound. The reaction is conducted in the presence of a solvent which is inert under the reaction conditions. Addition compounds are formed with the elimination of hydrogen chloride. The addition compounds are subsequently decomposed by heat into the desired isocyanate with the mixture also containing the active hydrogen compound. The monoisocyanate is subsequently removed by distillation.

29 Claims, No Drawings

PROCESS FOR THE PREPARATION OF AN ALIPHATIC MONOISOCYANATE

BACKGROUND OF THE INVENTION

It is known that isocyanates can be prepared by reacting amines with phosgene. This reaction proceeds via the carbamic acid chloride, which decomposes at elevated temperatures into the corresponding isocyanate and hydrogen chloride. If the boiling point of the isocyanate to be prepared is distinctly higher than the decomposition temperature of the carbamic acid chloride, the hydrogen chloride liberated by the decomposition reaction can easily be removed from the reaction, especially if an inert organic solvent is used. If, however, the decomposition temperature of the carbamic acid chloride is close to the boiling point of the isocyanate or above it, the isocyanate enters the vapor phase above the reaction mixture and recombines with the hydrogen chloride to reform carbamic acid chloride. Decomposition is therefore incomplete in such cases and the isocyanate is obtained in only low yield and is contaminated with carbamic acid chloride.

These conditions apply to aliphatic monoisocyanates in which the aliphatic groups contain from 1 to 4 carbon atoms, the greatest difficulties being encountered in the preparation of methyl isocyanate.

Several processes intended to overcome these difficulties have been described in the patent literature. A major proportion of these processes involve the decomposition of carbamic acid chlorides with the use of hydrogen chloride acceptors.

Thus, for example, it is known to prepare isocyanates from carbamic acid chlorides in the presence of organic bases, e.g., tertiary amines, or carboxylic acid dialkylamides as described in German Offenlegungsschrift No. 1,593,554 or tetraalkyl ureas as described in U.S. Pat. No. 3,644,461 in organic solvents. The use of water as described in German Auslegeschrift No. 2,156,761 and of aqueous solutions or suspensions of inorganic bases as described in British Pat. No. 1,208,862 for the absorption of hydrogen chloride has also been described. Olefins have also been mentioned as hydrogen chloride acceptors in German Offenlegungsschrift No. 2,210,285.

All these processes have the serious disadvantage of giving rise to by-products, in the form of corrosive organic or inorganic salts or alkyl chlorides, which must either be removed by expensive methods or contaminate the surroundings. Moreover, the use of organic bases involves the risk of side reactions leading to dimers and trimers. In the presence of water, a considerable proportion of the carbamic acid chloride is hydrolyzed to the amide hydrochloride so that satisfactory yields can be obtained only in the case of the comparatively unreactive tertiary butyl isocyanate.

The preparation of low boiling aliphatic monoisocyanates by thermal decomposition of carbamic acid chlorides in organic solvents by special technical procedures is also known.

According to German Auslegeschrift No. 1,193,034, thermal decomposition of carbamic acid chloride is carried out in a reactor equipped with a reflux condenser and separating column. Hydrogen chloride escapes through the reflux condenser while the isocyanate, carbamic acid chloride and solvent are held back. The isocyanate formed in the reaction enters the column and can be removed at the head of the column. Most of the isocyanate is returned by means of a reflux divider so that the hydrogen chloride ascending the column is completely absorbed and returns to the reactor in the form of carbamic acid chloride.

When this process is carried out continuously, solution depleted of carbamic acid chloride is continuously removed from the reactor to be enriched with carbamic acid chloride in another apparatus and then returned to the reactor.

Variations of this process have been described in U.S. Pat. Nos. 3,969,389; 3,991,094; 3,969,388; and 4,069,238. These variations are based on the same principle as described above and differ only in the apparatus used.

Although the processes mentioned above make it possible for low boiling aliphatic monoisocyanates to be produced by thermal decomposition of carbamic acid chlorides, they have the following disadvantages:

1. The removal of hydrogen chloride requires reflux condensers with large cooling surfaces, which must be operated at high energy cost with a large amount of cooling fluid so that the isocyanate and carbamic acid chloride will be retained quantitatively.

2. Removal of isocyanate free from carbamic acid chloride by distillation from the reaction mixture requires highly efficient fractionating columns and adjustment of the reaction to a high reflux ratio.

3. Satisfactory results can only be obtained if relatively dilute carbamic acid chloride solutions are used (1 to 30%).

4. In a continuous process (which is the only kind suitable for large-scale commercial production), the reaction solution must be repeatedly recirculated.

All this means that the reactants (isocyanate, carbamic acid chloride and solvent) must be repeatedly evaporated, condensed or cooled and reheated during the process, which entails high energy consumption. The use of dilute solutions and the necessity for repeated circulation result in a long dwelling time and hence low volume/time yields. The long dwelling time involves the risk of reduction in yield due to trimerization of the monoisocyanate. The process requires elaborate measuring and control techniques. This, together with the low volume/time yields and the necessity of using highly efficient fractionating columns result in high investment costs for commercial production.

DESCRIPTION OF THE INVENTION

The present invention provides a completely new method of obtaining low boiling aliphatic monoisocyanates from the corresponding carbamic acid chlorides in high yields without excessive expenditure in apparatus and without any substantial risk of recombination of hydrogen chloride with the monoisocyanate formed in the process.

The process of the instant invention comprises reacting carbamic acid chlorides with compounds having at least one active hydrogen atom so that adducts of the desired monoisocyanates are formed and hydrogen chloride is split off, and then decomposing these adducts by heat into the desired monoisocyanate with reformation of the original compound containing active hydrogen, which was used as auxiliary agent. This thermal decomposition of the adducts is accompanied by distillation to remove the decomposition products.

In this way, the hydrogen chloride liberated from the carbamic acid chlorides can be quickly and quantitatively removed in pure form from the reaction mixture at low temperatures without the aid of additional apparatus, and recombination of the isocyanate and hydrogen chloride to carbamic acid chloride cannot occur since the isocyanate is completely bound by chemical addition to the auxiliary agent used. The addition compound obtained, which is free from carbamic acid chloride, is subsequently decomposed at an elevated temperature, and the isocyanate thereby liberated can be easily and rapidly isolated in the pure form by distillation.

The present invention thus relates to a process for the preparation of a monoisocyanate of the formula

R—NCO, in which

R represents an aliphatic hydrocarbon group having from 1 to 4 carbon atoms, which may be olefinically unsaturated from the corresponding carbamic acid chloride of the formula R—NH—CO—Cl, in which the carbamic acid chloride is reacted with a compound having at least one active hydrogen atom in the presence of a solvent which is inert under the reaction conditions to form an addition compound of the isocyanate R—NCO and hydrogen chloride, which is liberated, and the addition compound is subsequently decomposed by heat into the desired isocyanate R—NCO and the aforesaid compound which has at least one active hydrogen atom, with the monoisocyanate formed in the reaction being at the same time separated by distillation from the compound which has at least one active hydrogen atom.

The carbamic acid chlorides used as starting compounds for the process according to the invention preferably are of the formula R—NH—CO—Cl in which R represents an aliphatic hydrocarbon group having from 1 to 4 carbon atoms, which may be olefinically unsaturated. In particular, R may represent a methyl, ethyl, n-propyl, iso-propyl, n-butyl, iso-butyl, sec.-butyl, tertiary butyl or propenyl group. R is preferably a methyl group.

Carbamic acid chlorides conforming to the above definition are obtained by a reaction of the corresponding amine R—NH$_2$, with phosgene, accompanied by liberation of hydrogen chloride. In the process according to the invention, the carbamic acid chloride may also be used as a mixture with an up to equimolar quantity of the corresponding monoisocyanate R—NCO. Such mixtures of carbamic acid chlorides with isocyanates are obtained by partial thermal liberation of hydrogen chloride from the corresponding carbamic acid chloride.

In the process according to the invention, the carbamic acid chlorides or mixtures of carbamic acid chlorides and isocyanates are preferably used as about 5 to 50% by weight solutions in organic solvents which are inert under the reaction conditions.

The following are examples of solvents which may be used: Aliphatic hydrocarbons such as pentane, hexane, heptane, octane, cyclohexane, and the like; halogenated aliphatic hydrocarbons such as methylene chloride, chloroform, carbon tetrachloride, n-propyl chloride, n-butyl chloride and the isomers thereof, amyl chloride, cyclohexyl chloride, ethylidene chloride, dichloroethylene, ethylene chloride, dichloropropane, dichlorobutane, isopropyl bromide, n-propyl bromide, butyl bromide, ethyl iodide, propyl iodide and fluorinated or partially fluorinated compounds; aromatic and substituted aromatic hydrocarbons such as benzene, toluene, xylene, ethyl benzene, chlorobenzene, dichlorobenzene, fluorobenzene, difluorobenzene, nitrobenzene and aromatic ethers; naphthalene derivatives such as chloronaphthalene; ketones such as acetone, methyl ethyl ketone, diethyl ketone or acetophenone; esters such as ethyl formate, alkyl esters of acetic acid, propionic acid esters, phthalic acid esters and other high boiling esters; other organic compounds such as carbon disulphide, methyl-tertiary butyl ether, ethyl propyl ether; tetrahydrofuran or acetonitrile. Mixtures of the above-mentioned solvents may, of course, also be used. Chlorobenzene and/or ethylene chloride are preferably used.

Organic compounds which contain at least one active hydrogen atom which are suitable for the process according to the invention are in particular those which (a) have a boiling point at least 20° C. above the temperature at which their addition compounds with aliphatic monoisocyanates split back to the original compound and (b) react with carbamic acid chlorides at temperatures within the range of about −20° C. to +130° C. form isocyanate addition compounds with liberation of hydrogen chloride and (c) whose addition compounds with aliphatic monoisocyanates decompose into the corresponding monoisocyanate and the active hydrogen compound itself at temperatures in the region of 100° C. to 250 C.

Three preferred groups of compounds which may be used as the compounds containing at least one active hydrogen atom include sulphuric or sulphonic acid amides, certain phenols, and certain urethanes.

The preferred temperatures within the above given ranges depends upon the actual compound used containing at least one active hydrogen atom.

For example, the preferred range for formation of the adduct using sulphuric acid or sulphonic amides is within the temperature range of −20° to +100° C. and the decomposition of the adduct takes place within the temperature range of 100° C. to 250° C. The corresponding temperature ranges using phenols or urethanes is −20° to +130° C. for formation of the adduct and 130° to 250° C. for decomposition of the adduct.

One of the preferred groups of compounds which fulfill the above conditions include those which have at least one group of the formula — SO$_2$—NHR$_1$ in which R$_1$ represents an aliphatic hydrocarbon group having from 1 to 20 preferably from 1 to 4 carbon atoms or an aromatic hydrocarbon group having from 6 to 14 preferably from 6 to 7 carbon atoms such as a phenyl or a p-tolyl group. These compounds have no other groups capable of reacting under the reaction conditions of the process according to the invention. Particularly peferred among these compounds are N-mono-substituted amides of sulphuric acid or of organic monosulphonic or polysulphonic acids of the formulae

SO$_2$(NHR$_1$)$_2$, R$_2$SO$_2$NHR$_1$, R$_3$(SO$_2$NHR$_1$)$_2$

In these formulae,

R$_1$ and R$_2$ represent an aliphatic hydrocarbon group having from 1 to 20 preferably from 1 to 4 carbon atoms or an aromatic hydrocarbon group having from 6 to 14 preferably 6 to 7 carbon atoms such as a phenyl or a p-tolyl group and $R_3$ represents an arylene group having from 6 to 15 carbon atoms preferably a phenylene group or an alkylene group having from 3 to 8 carbon atoms preferably a trimethylene group.

The following are typical examples of these particularly preferred compounds: N,N'-dimethyl sulphuric acid diamide, N,N'-dibutyl sulphuric acid diamide, N-ethyl-ethane sulphonic acid amide, N-methyl-benzene sulphonic acid amide, N-butyl-naphthalene sulphonic acid amide, N,N'-diethylbenzene-1,4-disulphonic acid amide and N,N-dipropyl-propane-1,3-disulphonic acid amide.

Suitable compounds having at least one group of the formula $-SO_2-NHR_1$ can be prepared from the corresponding acid chlorides, i.e., sulphuryl chloride or the chloride of organic sulphonic acids, and primary amines by a reaction accompanied by the liberation of hydrogen chloride.

Apart from the preferred or particularly preferred compounds mentioned above, reaction products of sulphuryl chloride or of organic sulphonic acid chlorides with primary diamines or polyamines may also be used for the process according to the invention. The following sulphonic acid chlorides, for example, may be used for preparing suitable auxiliary agents for the process of the invention: Aliphatic sulphonic acid chlorides, having from 1 to 12 carbon atoms such as methane sulphonic acid chloride, ethane sulphonic acid chloride, butane sulphonic acid chloride, octadecane sulphonic acid chloride, methane disulphonic acid chloride, or commercial mixtures of various sulphonic acid chlorides of the kind obtained from the sulphochlorination of aliphatic hydrocarbons (Ullmann, Volume 16, page 562). Aromatic sulphonic acid chlorides of benzene, toluene and naphthalene having from one to four sulphonic acid chloride groups may also be used.

The following are examples: Benzenesulphonic acid chloride, p-toluene sulphonic acid chloride, benzyl sulphonic acid chloride and benzene-1,3-disulphonic acid dichloride.

The following are examples of suitable primary amines: Methylamine, ethylamine, n-propylamine, isopropylamine, butylamine, ethylene diamine, propylene-1,2-diamine, propylene-1,3-diamine, 1,4-diamino butane, 1,6-diamino hexane, cyclohexylamine, aniline, and anilines having inert substituents on the nucleus.

Other suitable compounds containing at least one active hydrogen atom include any phenols containing, as substituents, at least one electrophilic group which increases the acidity of the phenolic hydroxyl group or groups, preferably at least one cyano-, nitro- or halo-substituent, which phenols are otherwise, that is to say apart from the hydroxyl group, inert under the reaction conditions of the process according to the present invention.

The phenols of this type used according to the present invention are preferably of the following general formula:

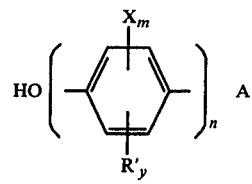

wherein

R' represents a hydroxyl group or an aliphatic hydrocarbon group having from 1 to 4 carbon atoms which may be olefinically unsaturated or which, together with a second group R', may form a condensed aromatic ring which may be substituted by other groups X and/or by other hydroxyl groups, A represents hydrogen, a group X, an aliphatic hydrocarbon group having from 1 to 3 carbon atoms or a sulphone group, $SO_2$, X represents cyano, nitro or halo, and preferably chlorine or nitro;

n represents 1 or 2, preferably 1;

m represents an integer of from 1 to 4, preferably 1 or 2, or, if the compound contains a condensed ring substituted with X or if n represents 2 and A represents $SO_2$, m may also represent 0; and y represents 0, 1 or 2.

The following are examples of such phenols: p-chlorophenol; 2,4-dichlorophenol; 2,4,6-trichlorophenol; pentachlorophenol; o-, m- and p-nitrophenol; 3-hydroxy benzonitrile; 4-hydroxy benzonitrile; 2-chloro-4-nitrophenol; 2-chloro-6-nitrophenol; 3-chloro-2-nitrophenol; 4-chloro-2-nitrophenol; 2-chloro-6-methylphenol; 6-chloro-3-methylphenol; 4-chloro-3-methylphenol; 2,4,6-trichloro-3-methylphenol; 4-chloro-1,3-dihydroxy benzene; 6-bromo naphthol-2; 2-chloronaphthol-1; 1-chloronaphthol-2; 8-chloronaphthol-2; 2,4-dichloronaphthol-1; 1-nitronaphthol-2; 8-nitronaphthol-2; 4,4'-sulphonyl-bis-phenol; 4,4'-(1-methyl ethylidene)-bis-(2,6-dichlorophenol); p-fluorophenol; p-bromophenol; 2,4,6-tribromophenol and p-iodophenol.

Other suitable compounds having at least one active hydrogen atom used in the process according to the present invention include any organic compounds which have at least one urethane group, NH—CO—O, and are otherwise inert under the reaction conditions of the process according to the present invention. Preferred urethanes of this type include, for example, those corresponding to the following general formula:

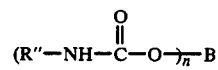

wherein

R" represents an optionally olefinically unsaturated aliphatic hydrocarbon group having from 1 to 10 carbon atoms or an aromatic hydrocarbon group having from 6 to 10 carbon atoms, preferably an optionally olefinically unsaturated aliphatic hydrocarbon group having from 1 to 4 carbon atoms with a methyl group being particularly preferred;

B represents an aliphatic hydrocarbon group having from 1 to 10 carbon atoms or a cycloaliphatic hydrocarbon group having from 5 to 10 carbon atoms; and n represents an integer of from 1 to 4.

Urethanes corresponding to the above general formula wherein R" corresponds to the substituent R of the carbamic acid chloride are particularly preferred because when these compounds are used, preparation of the auxiliary agent which is essential for the process according to the present invention may be carried out in situ by reaction of the carbamic acid chloride with the corresponding alcohol $B(OH)_n$.

Typical representatives of urethanes which are suitable for the purposes of the present invention are the reaction products of 1 mol or an isocyanate R"—NCO (or of a carbamic acid chloride R—NH—CO—Cl) with 1 mol of an alcohol $B(OH)_n$.

Apart from the isocyanates produced by the process according to the present invention, suitable monoisocyanates for the preparation of such urethanes include, n-hexylisocyanate, n-decylisocyanate, phenylisocyanate and 1-isocyanato-naphthalene. The following are examples of suitable alcohols $B(OH)_n$ for the preparation of the urethanes used according to the present invention; methanol, ethanol, n-propanol, isopropanol, n-butanol, isobutanol, n-hexanol, n-octanol, n-decanol, cyclohexanol, ethylene glycol, propane diol, butane diol, neopentyl glycol, hexane diol, glycerol, trimethylol propane and pentaerythritol.

The urethanes used in the process according to the present invention, may also include those prepared from polyfunctional isocyanates, such as hexamethylene diisocyanate, 2,4-diisocyanato toluene or 4,4'-diisocyanato diphenyl methane; and also monohydric alcohols, such as methanol or cyclohexanol. The only conditions which must be fulfilled by urethanes, if they are to be suitable for the process according to the present invention, is that they must contain at least one urethane group, NH—CO—O and, the boiling point thereof must be at least 20° C. above the decomposition point thereof.

The process according to the invention is generally carried out as follows:

A reaction between the compound having at least one active hydrogen atom and the carbamic acid chloride accompanied by liberation of hydrogen chloride, is carried out at a temperature within the range of from about −20° C. to +130° C. in the presence of a solvent of the kind mentioned above. The reactants are preferably mixed at room temperature and in such proportions that at least one active hydrogen atom of the active hydrogen compound and preferably from 1 to 1.5 active hydrogen atoms will be available per carbamic acid chloride group. When the starting materials have been mixed, the reaction, i.e., formation of the adduct with elimination of hydrogen chloride, is started by mild heating within the given temperature range, in the case of the sulphuric acid amides preferably to a temperature of about 60° to 80° C. and in the case of phenols and urethanes, preferably to a temperature of about 40° to 100° C. When at least 90% of the theoretically possible quantity of hydrogen chloride has split off and has escaped from the reaction vessel, the second stage of the reaction according to the invention, which is the thermal decomposition of the resulting addition product, is carried out. In the case of the phenols and urethanes, in order to remove remaining quantities of hydrogen chloride, it is preferred to raise the temperature to 130° C. prior to the second stage as the reaction. The thermal decomposition involves heating the reaction vessel to a temperature within the temperature range of, in the case of the sulphuric acid amides, from about 100° C. to 250° C. preferably to a temperature of about 130° to 160° C. In the case of the phenols temperatures of from about 160° C. to 180° C. are used, while for the urethanes temperatures of from about 180° to 200° C. are used. Under these conditions, the monoisocyanate formed distills off immediately. Depending on the boiling point of the solvent used, the distillate may consist of mixtures of the monoisocyanate with the solvent, in which case it must be redistilled for purification. If low boiling solvents are used, they distill off before the decomposition temperature of the adduct is reached, whereas if high boiling solvents are used, they are left in the reaction vessel. The major quantity of isocyanate is generally formed at a decomposition temperature of from about 130° to 160° C. when sulphuric acid amides are used, about 160° to 180° C. when phenols are used, and about 180° to 200° C. when urethanes are used. The sump temperature is raised to about 160°–250° C. preferably about 200° C. for sulphuric acid amides and phenols, and for urethanes 220° C. in order to complete the decomposition with reformation of the active hydrogen containing compound.

After separation of the isocyanate, the active hydrogen containing compound is obtained unchanged in the sump. A fresh quantity of carbamic acid chloride solution may be added and the process thus repeated several times. If this is intended, reformation of the active hydrogen containing compound is preferably not carried to completion so that the reactants will not be unduly subjected to heat.

It is clear from the above description that the process according to the invention is very suitable for continuous production. This can be carried out by arranging several reaction vessels in series, somewhat in the form of a cascade. The carbamic acid chloride solution and auxiliary agent are continuously mixed and fed into the first reaction vessel, where the major proportion of hydrogen chloride is split off at about 50° to 70° C. Elimination of hydrogen chloride is completed in the second reaction vessel at 70°–100° C. In the third and possibly subsequent reaction vessels, the isocyanate is liberated and distilled off together with solvent. The auxiliary agent is returned from the sump of the last reaction vessel to the starting point of the process. The isocyanate is isolated from the distillate or combined distillates by fractional distillation and the solvent, which may still contain carbamic acid chloride, is enriched with carbamic acid chloride elsewhere and returned to the process.

The aliphatic monoisocyanates obtainable by the process according to the invention are valuable starting compounds for the production of plant protective agents and pharmaceuticals.

EXAMPLES

EXAMPLE 1

In a four-necked flask 4 liters in capacity equipped with stirrer, contact thermometer and a packed column (height 30 cm, diameter 5 cm) with reflux divider a solution of 467.5 g (5 mol) of N-methyl-carbamic acid chloride in 500 ml of chlorobenzene is added to 1026 g (6 mol) of benzene sulphonic acid methylamide at 20° C. The temperature is raised to 100° C. over a period of one hour, during which time 98% of the calculated quantity of hydrogen chloride escapes through the column and reflux condenser attachment with the reflux divider closed, and is absorbed in water. The mixture is then heated to the reflux temperature of chlorobenzene (130° C.). Methyl isocyanate begins to split off at this temperature and is caused to escape together with chlorobenzene in the course of the next three hours by gradually raising the sump temperature to 200° C. with the reflux divider open. A mixture of 276 g (4.84 mol) of methylisocyanate, 5 g of N-methyl-carbamic acid chloride and 540 g of chlorobenzene is distilled off (crude yield 97%). Redistillation of this mixture yields 270 g (4.74 mol) of pure methylisocyanate (pure yield 94.7%) free from chlorine.

EXAMPLE 2

654 g (6 mol) of methane sulphonic acid methylamide are mixed with 467.5 g (5 mol) of N-methyl-carbamic acid chloride in 500 ml of chlorobenzene at 20° C. in the apparatus described in Example 1. 97% of the calculated quantity of hydrogen chloride are split off over a period of 90 minutes by gradual raising of the temperature to 100° C.

The reaction mixture is then gradually heated to 130° C. Methylisocyanate begins to distill off with the solvent at this temperature. When the temperature is gradually raised, 270.8 g of methylisocyanate (corresponding to 95% of the theory) are distilled off together with solvent over a period of four hours at temperatures of between 130 and 200° C. The yield after redistillation is 267.9 g of pure methylisocyanate (corresponding to 94% of the theory).

EXAMPLE 3

620 g (5 mol) of N,N'-dimethyl-sulphurylamide are reacted with 537.5 g (5 mol) of N-ethyl-carbamic acid chloride in 500 ml of o-dichlorobenzene in the manner described in Example 1. 319.5 g of ethyl isocyanate (corresponding to 90% of the theory) are obtained after decomposition of the adduct and redistillation of the mixture of isocyanate and solvent.

EXAMPLE 4

738 g (6 mol) of methane sulphonic acid ethylamide are reacted with 607.5 g (5 mol) of N-isopropyl-carbamic acid chloride in 500 ml of chlorobenzene in the manner described in Example 1. The yield of pure isopropyl isocyanate is 98% of the theory.

EXAMPLE 5

1110 g (6 mol) of p-toluene sulphonic acid methylamide are reacted with 607.5 g (5 mol) of N-propyl-carbamic acid chloride in 500 ml of xylene in the manner described in Example 1. The yield of pure n-propyl isocyanate is 96% of the theory.

EXAMPLE 6

1282.5 g (7.5 mol) of benzene sulphonic acid methylamide are reacted with 467.5 g (5 mol) of N-methyl-carbamic acid chloride in 500 ml of chlorobenzene at temperatures of up to 100° C. in the apparatus described in Example 1. The temperature is then raised to 160° C. over a period of thirty minutes and kept at this level for a further three hours. 300 ml of chlorobenzene are gradually added dropwise during this time. A mixture of isocyanate and solvent containing 3.5 mol of methylisocyanate (corresponding to 70% of the theory) distills off. When the sump has cooled down, 327.3 g (3.5 mol) of N-methyl-carbamic acid chloride are added in the form of a 50% solution in chlorobenzene and converted into methylisocyanate as already described.

The procedure is repeated a further four times, a quantity of N-methyl-carbamic acid chloride equivalent to the quantity of methylisocyanate obtained being added each time. The results are shown in the following Table.

| Reaction cycle | Quantity of carbamic acid chloride used in mol | Methyl-isocyanate in the distillate (in mol) |
| --- | --- | --- |
| 1 | 5 | 3.5 |
| 2 | 3.5 | 3.4 |
| 3 | 3.4 | 3.6 |
| 4 | 3.6 | 3.3 |
| 5 | 3.3 | 3.4 |
| 6 | 3.4 | 3.2 |

The total quantity of N-methyl-carbamic acid chloride used is 2075.7 g (22.2 mol). Redistillation of the combined distillates yields 1145.7 g (20.1 mol) of methylisocyanate (corresponding to 90.5% of the theory).

EXAMPLE 7

540 g (4.2 mol) of p-chlorophenol were mixed with 327.3 g (3.5 mol) of N-methyl-carbamic acid chloride in 600 ml of chlorobenzene at 20° C. in the apparatus described in Example 1. 99% of the calculated quantity of hydrogen chloride was split off by gradual raising of the temperature to 130° C. The reaction mixture was then heated to 160° C. Marked decomposition of methyl isocyanate set in at this temperature. The methyl isocyanate was distilled off together with chlorobenzene. The temperature was raised to 180° C. during distillation and maintained at this level for three hours. During this time, 150 g of methyl isocyanate (corresponding to 75% of the theoretical amount) distilled off together with chlorobenzene. The yield of pure product obtained after redistillation was 145.6 g of methyl isocyanate (corresponding to 73% of the theoretical yield).

EXAMPLE 8

684.6 g (4.2 mol) of 2,4-dichlorophenol were reacted with 376.3 g (3.5 mol) of N-ethyl-carbamic acid chloride in 600 ml of o-dichlorobenzene in a manner analogous to Example 7. 213.7 g of ethyl isocyanate (corresponding to 86% of the theoretical amount) were obtained after decomposition of the adduct and redistillation of the mixture of isocyanate and solvent.

EXAMPLE 9

827.4 g (4.2 mol) of 2,4,6-trichlorophenol were reacted with 425.3 g (3.5 mol) of N-isopropyl-carbamic acid chloride in 600 ml of chlorobenzene in a manner analogous to Example 7. The pure yield of isopropyl isocyanate was 270.7 g (corresponding to 91% of the theoretical yield).

EXAMPLE 10

729.1 g (4.2 mol) of 4-chloro-2-nitrophenol were reacted with 425.3 g (3.5 mol) of N-propyl-carbamic acid chloride in 800 ml of o-xylene in a manner analogous to Example 7. The yield of pure n-propyl isocyanate was 235 g (corresponding to 79% of the theoretical yield).

EXAMPLE 11

599 g (412 mol) of 4-chloro-3-methyl phenol were reacted with 327.3 g (3.5 mol) of N-methyl-carbamic acid chloride in 800 ml of o-dichlorobenzene in a manner analogous to Example 7. The pure yield of methyl isocyanates was 163.6 g (corresponding to 82% of the theoretical yield).

EXAMPLE 12

750.1 g (4.2 mol) of 2-chloronaphthol-1 were reacted with 376.3 g (3.5 mol) of N-ethyl-carbamic acid chloride in 600 ml of chlorobenzene in a manner analogous to Example 7. The yield of pure ethyl isocyanate was 191.3 g (corresponding to 77% of the theoretical yield).

EXAMPLE 13

1036.9 g (5.25 mol) of 2,4,6-trichlorophenol were reacted with 327.3 g (3.5 mol) of N-methyl-carbamic acid chloride in 500 ml of chlorobenzene in the apparatus described in Example 1. Hydrogen chloride was split off and the temperature at the end of the reaction was 130° C. The temperature was then raised to 180° C. within 30 minutes and maintained at this level for a further 3 hours. During this time, 300 ml of chlorobenzene were gradually added dropwise. A mixture of isocyanate and solvent containing 2.1 mol of methyl isocyanate (corresponding to 60% of the theoretical amount) distilled off. When the sump had cooled, 196.4 g (2.1 mol) of N-methyl-carbamic acid chloride were added in the form of a 50% solution in chlorobenzene and converted into methyl isocyanate as described above. The procedure was repeated three times, the quantity of carbamic acid chloride equivalent to the quantity of methyl isocyanate distilled off being replaced each time. A total of 9.6 mol of carbamic acid chloride was converted into 9.3 mol of methyl isocyanate (corresponding to 97% of the theoretical yield).

The results are shown in the following Table

| Reaction cycle | Quantity of Carbamic acid chloride used in mol | Methylisocyanate in in the distillate (mol) |
| --- | --- | --- |
| 1 | 3.5 | 2.1 |
| 2 | 2.1 | 2.2 |
| 3 | 2.2 | 1.8 |
| 4(*) | 1.8 | 3.2 |
| | 200° C. | |

(*)Final temperature:

EXAMPLE 14

550.2 g (4.2 mol) of N-methyl-carbamic acid butyl ester which had been prepared from N-methyl-carbamic acid chloride and n-butanol were reacted with 327.3 g (3.5 mol) of N-methyl-carbamic acid chloride in 500 ml of chlorobenzene with evolution of hydrogen chloride in a manner analogous to Example 7. The reaction mixture was then heated to 180° C., at which stage methyl isocyanate distilled off together with solvent. During this distillation, the temperature was raised to 200° C. within three hours. 175.6 g of methyl isocyanate (corresponding to 88% of the theoretical yield) were obtained after redistillation of the mixture of isocyanate and solvent.

EXAMPLE 15

726.6 g (4.2 mol) of N-ethyl-carbamic acid hexyl ester prepared from N-ethyl-carbamic acid chloride and n-hexanol were reacted with 376.3 g (3.5 mol) of N-ethyl-carbamic acid chloride in 500 ml of o-dichlorobenzene by a method analogous to that described in Example 14. The yield of pure ethyl isocyanate was 229.6 g (corresponding to 81% of the theoretical yield).

EXAMPLE 16

777 g (4.2 mol) of N-isopropyl-carbamic acid cyclohexyl ester prepared from N-isopropyl-carbamic acid chloride and cyclohexanol were reacted with 425.3 g (3.5 mol) of N-isopropyl-carbamic acid chloride in 500 ml of o-xylene in a manner analogous to Example 14. 223.1 g of isopropyl isocyanate (corresponding to 75% of the theoretical yield) were obtained.

EXAMPLE 17

575.4 g (2.1 mol) of bis-(N-propyl-carbamic acid)-neopentyl ester were reacted with 425.3 g (3.5 mol) of N-propyl-carbamic acid chloride in 800 ml of chlorobenzene in a manner analogous to Example 14. The yield of pure n-propyl isocyanate was 250 g (corresponding to 83% of the theoretical yield).

What is claimed is:

1. A process for the preparation of monoisocyanates of the formula

R—NCO from the corresponding carbamic acid chlorides of the formula

R—NH—CO—Cl in which
R represents an aliphatic hydrocarbon group having from 1 to 4 carbon atoms, which may be olefinically unsaturated,
comprising
(A) reacting said carbamic acid chloride with a compound having at least one active hydrogen atom selected from the group
consisting of
(1) amides of sulfuric acid or amides of organic sulfonic acids, said amides having the grouping

SO$_2$—NHR$_1$ in which
R$_1$ represents an aliphatic hydrocarbon group having from 1 to 20 carbon atoms or an aromatic hydrocarbon group having from 6 to 14 carbon atoms,
(2) phenols containing at least 1 electrophilic group which increases the acidity of the phenolic hydroxyl group under the reaction conditions of the process,
(3) urethanes which are otherwise inert under the reaction conditions,
in the presence of a solvent which is inert under the reaction conditions, said reaction resulting in the elimination of hydrogen chloride and the production of addition compounds,
(B) decomposing the addition compounds by heat to obtain the desired isocyanate and said active hydrogen compound, and
(C) removing the monoisocyanate by distillation.

2. A process according to claim 1, characterized in that the compounds which contain at least one active hydrogen atom (a) have a boiling point at least 20° C. above the temperature at which their addition compounds with aliphatic monoisocyanates split back to the original compound; (b) react with carbamic acid chlorides at temperatures within the range of about −20° C. to 130° C. to form isocyanate addition compounds with liberation of hydrogen chloride; and (c) whose addition compounds with aliphatic monoisocyanates decompose into the corresponding monoisocyanate and the active hydrogen compound itself at temperatures in the region of 100° C. to 250° C.

3. A process according to claim 1 characterized in that the carbamic acid chloride is N-methyl-carbamic acid.

4. A process according to claim 1, wherein the carbamic acid chloride and the active hydrogen compound are mixed at room temperature and in such proportions that at least one active hydrogen atom of the active hydrogen compound will be available per carbamic acid chloride group.

5. The process according to claim 1, characterized in that the carbamic acid chlorides are used as about 5 to 50% by weight solutions in their inert solvents.

6. A process according to claim 5, characterized in that the inert solvent is chlorobenzene.

7. A process according to claim 5, characterized in that the inert solvent is ethylene chloride.

8. A process according to claim 1, wherein the reaction between the compound having at least one active hydrogen atom and the carbamic acid chloride is carried out at a temperature within the range of from −20° C. to 100° C.

9. A process according to claim 8, wherein from 1 to 1.5 active hydrogen atoms are available per carbamic acid chloride group.

10. A process according to claim 9, wherein said decomposing temperature is within the range of from about 130° C. to about 160° C.

11. A process according to claim 1, characterized in that the decomposing of the addition compounds is accomplished by heating to a temperature of from about 100° C. to about 250° C.

12. A process according to claim 11, wherein said addition compound is heated to from about 130° C. to about 160° C. and thereafter temperature is raised to from about 160° C. to about 250° C. in order to complete the decomposition.

13. A process according to claim 1, characterized in that the amides of sulphuric acid or amides or organic sulphonic acids react with carbamic acid chlorides at temperatures within the range of about 60° to 80° C.

14. A process according to claim 1, wherein the said amides having the grouping —SO$_2$—NHR$_1$ are selected from the group consisting of SO$_2$(NHR$_1$)$_2$, R$_2$SO$_2$NHR$_1$, and R$_3$(SO$_2$NHR$_1$)$_2$ wherein R$_1$ and R$_2$ represent an aliphatic hydrocarbon group having from 1 to 20 carbon atoms or an aromatic hydrocarbon group having from 6 to 14 carbon atoms in which R$_1$ and R$_2$ may be the same or different, and R$_3$ represents an arylene group having from 6 to 15 carbon atoms or an alkylene group having from 3 to 8 carbon atoms.

15. A process according to claim 14, characterized in that R$_1$ and/or R$_2$ represent an aliphatic hydrocarbon group having from 1 to 4 carbon atoms.

16. A process according to claim 1, wherein said phenols are characterized by the following general formula:

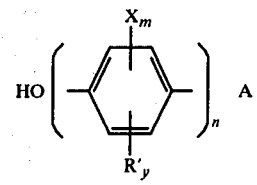

wherein
R′ represents a hydroxyl group or an aliphatic hydrocarbon group having from 1 to 4 carbon atoms which may be olefinically unsaturated or which, together with a second group R′, may form a condensed aromatic ring which may be substituted by other groups X and/or by other hydroxyl groups,
A represents hydrogen, a group X, an aliphatic hydrocarbon group having from 1 to 3 carbon atoms or a sulphone group, SO$_2$,
X represents cyano, nitro or halo,
n represents 1 or 2,
m represents an integer of from 1 to 4, preferably 1 or 2, or, if the compound contains a condensed ring substituted with X or if n represents 2 and A represent SO$_2$, m may also represent 0; and
y represents 0, 1 or 2.

17. A process according to claim 1, wherein said phenol is selected from the group consisting of p-chlorophenol; 2,4-dichlorophenol; 2,4,6-trichlorophenol; 4-chloro-2-nitrophenol; 4-chloro-3-methyl phenol; and 2-chloronapthol-1.

18. A process according to claim 1, wherein X represents chlorine or nitro and n represents the integer 1.

19. A process according to claim 1, characterized in that the phenols react with carbamic acid chlorides at temperatures within the range of about 40° to 100° C.

20. A process according to claim 19 in that after 90% of the theoretically possible quantity of hydrogen chloride has split off, the remaining hydrogen chloride is removed by heating to about 130° C.

21. A process according to claim 1, wherein said urethanes are characterized by the following general formula:

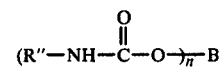

wherein
R″ represents an optionally olefinically unsaturated aliphatic hydrocarbon group having from 1 to 10 carbon atoms or an aromatic hydrocarbon group having from 6 to 10 carbon atoms,
B represents an aliphatic hydrocarbon group having from 1 to 10 carbon atoms or a cycloaliphatic hydrocarbon group having from 5 to 10 carbon atoms; and
n represents an integer of from 1 to 4.

22. A process according to claim 21, wherein R″ represents an olefinically unsaturated aliphatic hydrocarbon group having from 1 to 4 carbon atoms, a methyl group being particularly preferred.

23. A process according to claim 1, characterized in that the urethanes react with carbamic acid chlorides at temperatures within the range of 40° to 100° C.

24. A process according to claim 21, characterized in that after 90% of the theoretically possible quantity of hydrogen chloride has split off, the remaining hydrogen chloride is removed by heating to about 130° C.

25. The process of claim 1 wherein, when the compounds having at least one active hydrogen atom are amides of sulfuric acid or of organic sulfonic acids, the monoisocyanate is distilled off at temperatures of about 130° to 160° C.

26. The process of claim 1 wherein, when the compounds which contain at least one active hydrogen atom are phenols containing at least one electrophilic group, the monoisocyanate is distilled off at temperatures of about 160° to 180° C.

27. The process of claim 21 wherein said urethane groups are prepared from isocyanates selected from the group consisting of N-hexylisocyanate, N-decylisocyanate, phenylisocyanate, and 1-isocyanato-naphthalene.

28. The process of claim 1 wherein, when urethanes are used as the compounds which contain at least one active hydrogen atom, the monoisocyanate is distilled off at temperatures about 180° to 200° C.

29. The process of claim 1 wherein said phenols containing at least one electrophilic group which increase the acidity of the phenolic hydroxyl groups is represented by the formula:

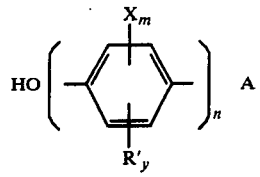

wherein
$R'$ represents hydrogen or a methyl group
A represents hydrogen
X represents Cl
n represents 1
m represents an integer of from 1 to 3
y represents 0, 1 or 2.

* * * * *